(12) United States Patent

Otsuka

(10) Patent No.: US 8,710,436 B2
(45) Date of Patent: Apr. 29, 2014

(54) IONIZATION DEVICE, MASS SPECTROMETER INCLUDING THE IONIZATION DEVICE, AND IMAGE GENERATION SYSTEM INCLUDING THE IONIZATION DEVICE

(71) Applicant: Canon Kabushiki Kaisha, Tokyo (JP)

(72) Inventor: Yoichi Otsuka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/016,944

(22) Filed: Sep. 3, 2013

(65) Prior Publication Data

US 2014/0070088 A1 Mar. 13, 2014

(30) Foreign Application Priority Data

Sep. 7, 2012 (JP) ................................. 2012-197209

(51) Int. Cl.
*G01N 1/22* (2006.01)
(52) U.S. Cl.
CPC ......................................... *G01N 1/22* (2013.01)
USPC ..................................... 250/288; 250/423 R
(58) Field of Classification Search
USPC ............................................. 250/288, 423 R
See application file for complete search history.

(56) References Cited

U.S. PATENT DOCUMENTS

| 7,902,499 B2 * | 3/2011 | Hiraoka et al. | 250/282 |
| 7,910,881 B2 | 3/2011 | Nikolaev | |
| 8,519,330 B2 * | 8/2013 | Van Berkel et al. | 250/288 |
| 2013/0206976 A1 * | 8/2013 | Verbeck, IV | 250/282 |

OTHER PUBLICATIONS

Roach, et al., "Nanospray desorption electrospray ionization: an ambient method for liquid-extraction surface sampling in mass spectrometry", The Royal Society of Chemistry Analyst, 2010, 4 pp. 2233-2236, vol. 135.

* cited by examiner

*Primary Examiner* — Kiet T Nguyen
(74) *Attorney, Agent, or Firm* — Canon USA Inc. IP Division

(57) ABSTRACT

An ionization device includes a support configured to support a sample, a probe configured to determine a portion of the sample to be ionized, an irradiation unit configured to emit laser light and is disposed to irradiate with the laser light a liquid bridge portion between the sample and the probe, an extract electrode configured to extract ions obtained by ionizing the sample, a liquid supply unit configured to supply a liquid to a region of the sample, and voltage application units configured to generate an electric field between a portion of the probe that is in contact with the liquid bridge portion and the extract electrode.

16 Claims, 5 Drawing Sheets

IONIZATION DEVICE, MASS SPECTROMETER INCLUDING THE IONIZATION DEVICE, AND IMAGE GENERATION SYSTEM INCLUDING THE IONIZATION DEVICE

BACKGROUND OF THE INVENTION

1. Field of the Invention

The present invention relates to ionization devices for ionizing samples. Ionization devices described herein may be particularly useful in mass spectrometry imaging.

2. Description of Related Art

There exists a technique for ionizing a solid sample in an atmospheric pressure environment in order to analyze components in the surface of the solid sample.

In addition, research is being performed in the field of imaging mass spectrometry (IMS), in which, with the use of an ionization technique, an image that indicates the types of substances present on the surface of a sample and their locations on the surface is displayed.

Patrick J. Roach, et al., "Nanospray desorption electrospray ionization: an ambient method for liquid extraction surface sampling in mass spectrometry" Analyst, 135, pp. 2233-2236 (2010) and U.S. Pat. No. 7,910,881 each discuss a method in which a solvent is applied to a fine region of a solid surface in an atmospheric pressure environment and substances (solutes) that have dissolved in the solvent are ionized.

The method discussed by Patrick J. Roach, et al. uses two capillaries. The two capillaries are disposed such that ends of the respective capillaries are positioned in close proximity to each other. The solvent is supplied from one of the capillaries, and the other capillary transports the solvent that contains a solute from the solid (i.e., solution) to an ionization section. A high voltage is applied to the solution in the ionization section, and thus the solute is ionized at the end of the other capillary.

The method discussed in U.S. Pat. No. 7,910,881, meanwhile, uses a capillary having a double-tube structure. The solvent is discharged to an end of the capillary from a portion between an outer tube and an inner tube. The inner tube is at a negative pressure and thus is capable of suck in the discharged solvent in which the solute has dissolved (i.e., solution). This capillary is brought close to the surface of the sample, and the surface of the sample is irradiated with laser light. Thus, desorbed substances can be dissolved in the liquid at the end of the capillary. The solution containing the solute moves through the inner tube and is introduced into a mass spectrometer.

According to the method discussed in Patrick J. Roach, et al., although ionization is carried out in an atmospheric pressure environment, only a substance that easily dissolves in the solvent can dissolve as a solute in the solvent, which leaves room for improvement. Meanwhile, according to the method discussed in U.S. Pat. No. 7,910,881, as the sample is irradiated with the laser light, a substance that does not easily dissolve in the solvent can dissolve in the solvent. However, since a process of taking a substance into the solvent (i.e., sampling process) and a process of causing ionization (i.e., ionization process) are carried out in separate locations, and a time lag exits between the sampling process and the ionization process. Thus, it is difficult to carry out the analysis at high speed.

SUMMARY OF THE INVENTION

An exemplary embodiment of the present invention is directed to achieving high ionization efficiency by causing a substance that does not easily dissolve in a solvent in an atmospheric pressure environment to actively dissolve in the solvent.

According to an aspect of the present invention, an ionization device includes a support configured to support a sample, a probe configured to determine a portion of the sample to be ionized, an irradiation unit configured to emit laser light and is disposed to irradiate with the laser light a liquid bridge portion between the sample and the probe, an extract electrode configured to extract ions obtained by ionizing the sample, a liquid supply unit configured to supply a liquid to a region of the sample, and an electric field generation unit configured to generate an electric field between a portion of the probe that is in contact with the liquid bridge portion and the extract electrode.

Further features of the present invention will become apparent from the following description of exemplary embodiments with reference to the attached drawings.

DESCRIPTION OF THE EMBODIMENTS

First Exemplary Embodiment

An ionization device according to a first exemplary embodiment of the present invention includes a liquid supply unit configured to supply a solvent to a sample, a probe configured to form a liquid bridge between the sample and the probe, and an irradiation unit disposed to irradiate a liquid bridge portion with laser light.

Figure 1:
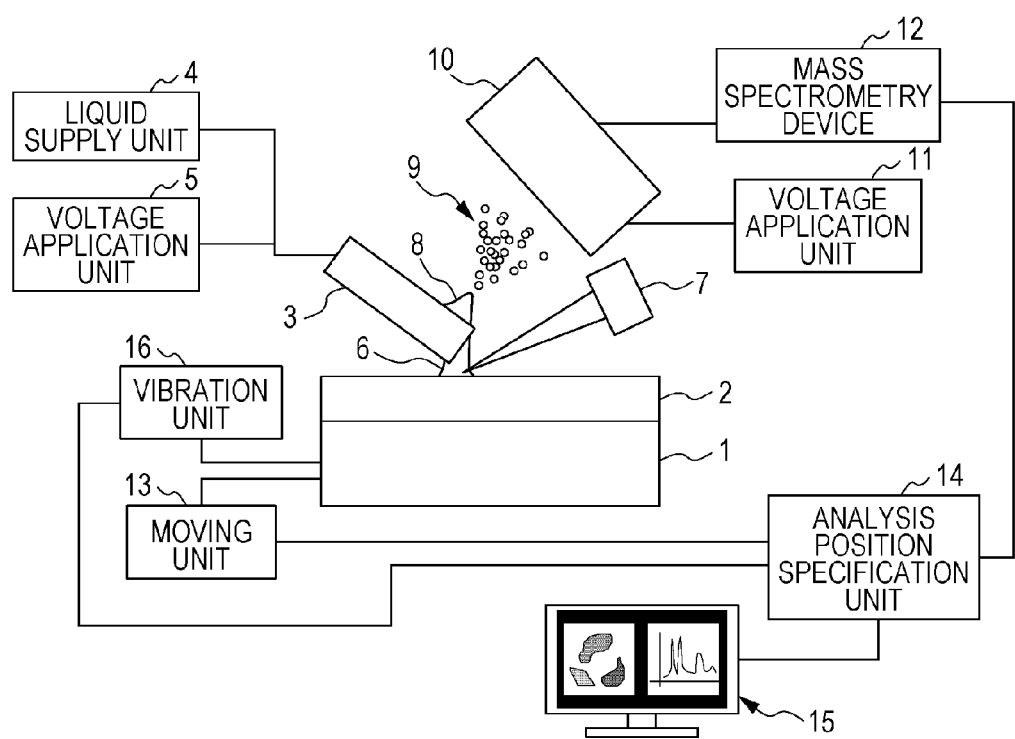
FIG. 1 is a schematic diagram illustrating an image generation system that includes an ionization device according to a first exemplary embodiment.

FIG. 1 is a schematic diagram illustrating an image generation system that includes the ionization device according to the first exemplary embodiment of the present invention.

A sample 2 is placed on and is supported by a support 1. The support 1 may also be referred to as a sample holder or sample stage, and may include, for example, a thin-layer chromatographic plate, a silicone-based translucent mould slide, or the like, as it is known to persons having ordinary skill in the art. The sample 2 is a section (cell group) of biological tissue, for example. A probe 3 is, for example, a needle-shaped instrument which is disposed such that one end thereof is in contact with or, as illustrated in FIG. 1, is in close proximity to the sample 2. A flow channel (not illustrated) is formed inside the probe 3, and a solvent is supplied to the surface of the sample 2 through the flow channel. The solvent is a liquid in which a substance contained in the sample 2 can dissolve as a solute, and the solvent in which the solute has dissolved is referred to as a solution, hereinafter. The solvent is preferably a mixture of water and an organic solvent. Although it is preferable that at least any one of an acid and a base is further mixed in the mixture, only water or an organic solvent can serve as the solvent. As this mixture serving as the solvent makes contact with the sample 2, a substance (for example, at least one of a lipid, a saccharide, and a molecular compound having a mean molecular weight of 20 or more but less than a hundred million) contained in the sample 2 that easily dissolves in the solvent readily dissolves in the mixture. Therefore, the liquid serving as the solvent changes into a solution.

Here, "dissolving in a solvent" refers to a state where molecules, atoms, and fine particles of a substance are dispersed in the solvent. Examples of substances that easily dissolve include a lipid molecule forming a cell membrane, a saccharide contained in a cell, and a floating protein. Examples of substances that do not easily dissolve include a protein forming the cytoskeleton and a protein anchored to the cytoskeleton.

The solvent is supplied continuously from a liquid supply unit 4 to the probe 3, and a voltage is applied to the solvent, while being supplied, by a voltage application unit 5. The solvent that has been supplied to the probe 3 then forms a liquid bridge 6 between an end portion of the probe 3 and the sample 2. A "liquid bridge" refers to the formation of a liquid connection that bridges a space between the probe 3 and the sample 2. Such a liquid bridge may be formed by surface tension. Formation of the liquid bridge 6 allows a substance in the surface of the sample 2 to dissolve in the liquid. The liquid bridge 6 is formed in an atmospheric pressure environment. The liquid bridge 6 has a small volume of approximately $1 \times 10^{-12}$ m$^3$. The area of the liquid bridge 6 along an in-plane direction of the sample 2 is approximately $1 \times 10^{-8}$ m$^2$. That is, the liquid bridge 6 is formed on a part of the surface of the sample 2.

An irradiation unit 7 that emits laser light includes a light source arranged such that the laser light impinges on the liquid bridge 6. A region of the liquid bridge 6 that is to be irradiated with the laser light is referred to as a liquid bridge portion. The liquid bridge portion may include a part of the liquid bridge 6 or the entire liquid bridge 6.

The irradiation unit 7 is disposed at a side of the sample 2, that is, at a side of the support 1 where the sample 2 is to be placed. The support 1 includes a vibration unit 16, and the vibration unit 16 causes the liquid bridge 6 to vibrate.

As a system for checking a focus position of the laser light, a camera for observing an irradiation spot may be included in the irradiation unit 7. Then, by observing light from the focus position with the camera and by adjusting the position of the irradiation unit 7 or the probe 3 so that the position of the liquid bridge portion coincides with the focus position of the laser light, the liquid bridge portion can be irradiated with the laser light efficiently. When observing the liquid bridge portion, it is preferable to stop the emission of the laser light or to use an optical filter that does not transmit light in the wavelength band of the laser light. When observing the focus position of the laser light, it is preferable to use an optical filter that transmits light in the wavelength band of the laser light. A positioning device such as a stepping motor is preferably used to adjust the position of the irradiation unit 7 or the probe 3, and such a positioning device can be connected to a support unit of the irradiation unit 7 or the probe 3.

The spot size of the laser light on the surface of the sample 2 has an area of approximately $1 \times 10^{-12}$ m$^2$ or greater. The spot size can be changed as desired depending on the laser light focusing lens (not illustrated) and can be set to be greater than the area of the liquid bridge portion. A drive unit for driving the light source to emit pulsed laser light is preferably provided, and pulsed laser light having a pulse duration in the femtosecond to nanosecond range and a power of 10 J/m$^2$ or greater is preferably used. The wavelength of the laser light may be in any of an ultraviolet range, a visible range, and an infrared range.

An ion extract electrode 10 and a voltage application unit 11 for applying a voltage to the ion extract electrode 10 are provided in order to generate a Taylor cone 8 at a leading end of the probe 3. A large potential difference (1 kV or more but 10 kV or less, or preferably 3 kV or more and 5 kV or less) between the liquid on the probe 3 and the ion extract electrode 10 causes the liquid to form the Taylor cone 8. The Taylor cone 8 is conical in shape with its apex oriented toward an ion take-in port. The charged liquid at the apex of the Taylor cone 8 is pulled off the Taylor cone 8 to form highly charged liquid droplets 9, and the charged liquid droplets 9 are then sprayed toward the ion extract electrode 10. This liquid includes the solvent in which a substance contained in the sample 2 has dissolved as a solute.

The substance contained in the liquid droplets 9 is introduced into a mass spectrometer in an ionized state. The mass spectrometer measures a mass-to-charge ratio of ions. Note that a series of processes including formation of the Taylor cone 8, spraying of the charged liquid droplets 9, and ionization is referred to as electrospray ionization, hereinafter.

The liquid bridge 6 is connected to the Taylor cone 8. The aforementioned substance dissolves in the liquid bridge 6 even when electrospray ionization is under way. The charged liquid is supplied continuously to the probe 3, and spraying occurs continuously. Formation of the liquid bridge 6 and ionization of the substance are carried out with the single probe 3.

As the liquid bridge portion is irradiated with the laser light as in the first exemplary embodiment, a solute that does not easily dissolve in a mixture serving as the solvent containing water, an organic solvent, and an acid or a base can dissolve in the mixture in large quantity. Accordingly, the Taylor cone 8 includes both a solute that easily dissolves in the solvent and a solute that does not easily dissolve in the solvent.

In the first exemplary embodiment, the laser light is used to allow a substance that does not easily dissolve in the solvent to dissolve in the solvent. Alternatively, in an ionization device according to an exemplary embodiment of the present invention, the laser light may be used for ionization after the solute is irradiated with the laser light to undergo a photochemical reaction. To be more specific, a photocatalytic reaction, an optical sectioning reaction, or an optical absorption reaction is used. In the first exemplary embodiment, once the liquid forming the liquid bridge 6 is irradiated with the laser light, the liquid promptly undergoes electrospray ionization, and thus it is possible to analyze, for example, a substance having a short lifetime of 1 millisecond or less (radical molecule, reaction intermediate).

The ion extract electrode 10 includes a conductive member and is connected to the voltage application unit 11, and a predetermined voltage is applied to the ion extract electrode 10 by the voltage application unit 11. The ion extract electrode 10 is a structural member for forming a flow path through which ions contained in the liquid droplets 9 that are separated from the Taylor cone 8 are taken in and, for example, is cylindrical in shape. A pump (not illustrated) is connected to the ion extract electrode 10, and the ions are attracted to the ion extract electrode 10 along with an outside environment, that is, a surrounding gas. The ions pass through the ion extract electrode 10 in a liquid state or in a gaseous state. Then, the ions fly in a gaseous state in a mass spectrometry device 12. The mass spectrometry device 12 is a time of flight (TOF) mass spectrometer that utilizes a TOF method.

The ions fly through a vacuum flight space within the mass spectrometry device 12 and have their masses analyzed.

Here, by applying a voltage to the solvent intermittently, an electrospray can be generated intermittently. This configuration makes it possible to ionize a substance while limiting duration for which a voltage is applied to the substance that undergoes a change in its characteristics due to a voltage being applied to a minimum.

That is, the use of the ionization device according to the first exemplary embodiment makes it possible to form the liquid bridge portion that links the probe 3 and the sample 2 with the liquid disposed on the surface of the sample 2, to irradiate the liquid bridge portion with the laser light, and to spray the liquid on the probe 3 for carrying out mass spectrometry on the ionized substance, which in turn enables a sample analysis that excels in ionization in an atmospheric pressure environment, that is, a sample analysis with high sensitivity.

An image generation system according to the first exemplary embodiment includes a mass spectrometer and an image information generation device. The mass spectrometer includes an ionization unit and the mass spectrometry device 12. The ionization unit corresponds to the ionization device that includes the support 1, the probe 3, the irradiation unit 7, the ion extract electrode 10, the liquid supply unit 4, and the voltage application units 5 and 11.

As stated above, the liquid bridge 6 is formed in an extremely small region on the surface of the sample 2. In order to analyze a larger area of the surface of the sample 2, a moving unit 13 for moving the sample 2 in the in-plane direction thereof is provided. The moving unit 13 is connected to an analysis position specification unit 14, and the analysis position specification unit 14 is connected to the mass spectrometry device 12. The analysis position specification unit 14 specifies a region to be analyzed by the mass spectrometry device 12 as positional information and moves the support 1 so that a solute present at the specified position is contained in the liquid bridge 6 and then in the Taylor cone 8. The result of mass spectrometry is obtained in the form of mass information such as mass spectral data by the mass spectrometry unit 12. The analysis position specification unit 14 corresponds to the aforementioned image information generation device. The image information generation device includes an image generation unit that generates image information to be used to display an image on the basis of the result of mass spectrometry performed on the target substance at the specified position. The image information may be for a two-dimensional image or a three-dimensional image. The image information outputted from an output unit (not illustrated) of the analysis position specification unit 14 is sent to an image display unit 15 such as a flat panel display connected to the analysis position specification unit 14. The image information is inputted to the image display unit 15 and displayed in the form of an image. In this manner, carrying out mass spectrometry at multiple positions while changing the specified position along the surface of the sample 2 on the basis of the result of mass spectrometry performed on the specified position makes it possible to display the results of mass spectrometry performed on the sample 2 in the form of an image. In other words, the component distribution of substances contained in the sample 2 is displayed in the form of an image on the basis of the analyzed mass information and the positional information of the sample 2. Components in the solute dissolving in the liquid bridge 6 can be found from the result of mass spectrometry. A predetermined component in the biological tissue section is mapped in the image (multilayered display). In addition to the position of the component, the amount of the component is also displayed, and differences in the amount are indicated by varying colors or brightness. Further, it is also possible to display a superimposed image of a microscopic image of the sample 2 obtained in advance and an image indicating the obtained mass of the sample 2.

The analysis position specification unit 14 is connected to the vibration unit 16. In the first exemplary embodiment, laser light and vibration are used in combination in order to allow a solute that does not easily dissolve in the solvent to dissolve in the solvent.

The vibration unit 16 is configured to cyclically change the relative distance between the probe 3 and the sample 2, and increasing or decreasing the relative distance makes it possible to improve the ionization efficiency of the sample 2.

The moving unit 13 is not particularly limited as long as the moving unit 13 can change the position on the sample 2 at which the liquid bridge 6 is formed between the sample 2 and the probe 3 and the position that is irradiated with the laser light relative to each other.

As illustrated in FIG. 1, in a state where the spatial disposition of the irradiation unit 7 and the probe 3 is fixed, the support 1 for the sample 2 may be moved by a moving mechanism. Alternatively, in a state where the sample 2 is fixed, a unit configured to move the irradiation unit 7 and the probe 3 may be provided. In either configuration, it is preferable to move the position where the sample 2 is analyzed in a state where the positional relationship between the irradiation unit 7 and the probe 3 is retained, that is, in a state where the irradiation unit 7 and the probe 3 are fixed.

The ionization device according to the first exemplary embodiment uses a biological tissue section as a sample, a mixture containing water, an organic solvent, and an acid or a base as a solvent, at least any one of a lipid, a saccharide, and a molecule having a mean molecular weight of 20 or more but less than a hundred million as a solute that easily dissolves in the solvent, and a high molecule having a mean molecular weight of 20 or more but less than a hundred million as a solute that does not easily dissolve in the solvent. However, an ionization device according to an exemplary embodiment of the present invention can be applied to other combinations of a sample, a solvent, and a solute. For example, the ratio of water, an organic solvent, and an acid or a base in a solvent can be varied. One of the components in a given ratio may, for example, be 0, that is, one of the components may not be contained. Varying the ratio allows solubility, in the mixture, of a water-soluble molecule and a fat-soluble molecule contained in the sample 2 to be varied, and thus ionization of a desired molecule can be prioritized.

In the ionization device according to the first exemplary embodiment, the voltage application unit 5 applies a voltage to the solvent, and in this case the probe 3 is preferably an insulator. Alternatively, an ionization device according to an exemplary embodiment of the present invention may be configured such that the voltage application unit 5 applies a voltage to the probe 3 and, as a result, the voltage is applied to the solvent. In this case, the probe 3 is preferably formed of a conductor, and the solvent is disposed so as to be in contact with the conductor.

In the ionization device according to the first exemplary embodiment, the probe 3 has a flow channel formed therein, and the solvent flows in the flow channel. Alternatively, an ionization device according to an exemplary embodiment of the present invention may be configured such that the liquid supply unit 4 supplies liquid droplets to the probe 3 and the liquid droplets flow along the probe 3 to the leading end thereof so as to form the liquid bridge 6.

In the ionization device according to the first exemplary embodiment, the probe 3 has a flow channel formed therein. Alternatively, an ionization device according to an exemplary embodiment of the present invention may include a plurality of flow channels, and distinct solvents may flow in the respective flow channels. In this case, a unit configured to apply distinct voltages to the respective solvents may be provided.

In the ionization device according to the first exemplary embodiment, the ion extract electrode 10 is connected to the voltage application unit 11 that is configured to apply a voltage to the ion extract electrode 10. In this case, the ion extract electrode 10 preferably includes a conductive member, and this conductive member is preferably connected to the voltage application unit 11.

Alternatively, an ionization device according to an exemplary embodiment of the present invention may be configured such that the ion extract electrode 10 is formed of an insulator and a conductive member is disposed on the ion extract electrode 10 at an end that is close to the probe 3. Then, the voltage application unit 11 may be connected to the conductive member so as to apply a high-voltage electric field to the Taylor cone 8, the liquid droplets 9, and gaseous ions.

The ion extract electrode 10 of the first exemplary embodiment is provided with a pump (not illustrated), but it is possible to take the ions into the mass spectrometer only by utilizing an attraction effect of the electric field without operating the pump.

In the ionization device according to the first exemplary embodiment, the irradiation unit 7 is disposed at a side of the support 1 where the sample 2 is placed on. Alternatively, in an ionization device according to an exemplary embodiment of the present invention, the irradiation unit 7 may be disposed at a side of the sample 2 that is behind the side that faces the probe 3. In this case, the liquid bridge portion is irradiated with the laser light that has passed through the sample 2. The support 1 may be provided at an edge of the sample 2 so as not to be provided in an optical path of the laser light. Alternatively, the support 1 may be formed by a light transmissive member that does not hinder passage of the laser light.

The ionization device according to the first exemplary embodiment may be used as an ion generation unit not only of a TOF mass spectrometer but also of a quadrupole mass spectrometer, a magnetic field deflection mass spectrometer, ion trap mass spectrometer, and ion cyclotron mass spectrometer.

In the ionization device according to the first exemplary embodiment, the liquid bridge 6 is formed in an atmospheric pressure environment and the substance is ionized. Here, the atmospheric pressure covers a range of 0.1 to 10 times the standard atmospheric pressure of 101325 Pa. Alternatively, the environment may be in an atmosphere that is the same as a typical room environment, or in an inert gas atmosphere such as a nitrogen atmosphere or an argon atmosphere.

The ionization device according to the first exemplary embodiment is configured such that the solvent continuously flows through the flow channel formed in the probe 3 at a constant flow rate. Alternatively, the flow rate (flow speed) of the solvent may be controlled. That is, an increase or a decrease in the flow rate can be set as desired. Thus, by increasing the flow rate if the amount of a substance to be dissolved is large or decreasing the flow rate if the amount of the substance is small, a fluctuation in the concentration of a substance dissolved in the liquid bridge 6 can be suppressed, and the substance in the sample 2 can be ionized efficiently. Varying the flow rate also makes it possible to vary the size of the liquid bridge 6. The size of the liquid bridge 6 corresponds to the size of an ionization region and thus correlates with spatial resolution of a mass image. A smaller liquid bridge 6 leads to improved spatial resolution but increases the number of regions to be measured, and thus a total measurement time increases. That is, varying the flow rate makes it possible to vary the total measurement time. For example, after a mass image is obtained at low spatial resolution, an area in the mass image can be specified. Then, a detailed mass image of the specified area can be obtained at higher spatial resolution.

In the ionization device according to the first exemplary embodiment, the liquid bridge 6 is irradiated with the laser light continuously. Alternatively, the liquid bridge 6 may be irradiated with the laser light intermittently during a given period of time. That is, the liquid bridge 6 may be irradiated with the laser light for a given period of time, and then the irradiation may be stopped for another given period of time. For example, the ionization efficiency of a sample 2 in which both a substance that is easily decomposed by the laser light and a substance that is not easily decomposed by the laser light are present can be improved by pausing the irradiation of the laser light while the substance that is easily decomposed by the laser light undergoes ionization and by irradiating the sample 2 with the laser light while the substance that is not decomposed by the laser light undergoes ionization.

Figure 3:
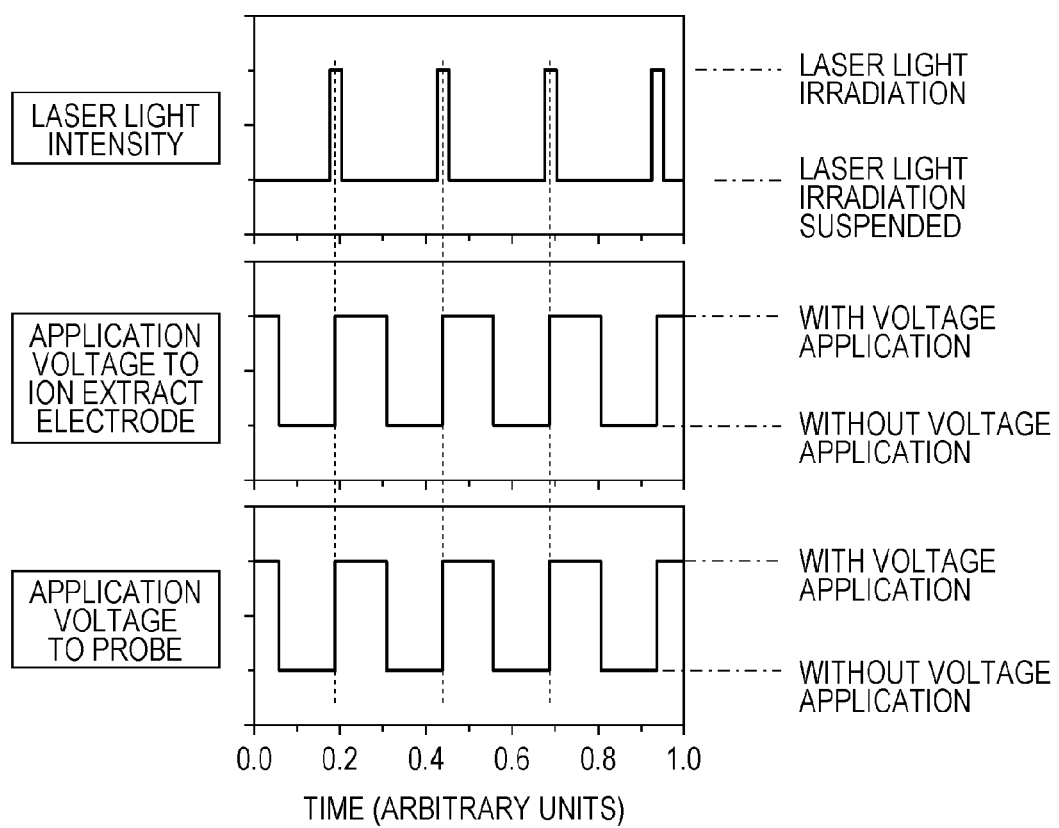
FIG. 3 is a schematic diagram illustrating timings of laser light irradiation and voltage application in the ionization device according to the first exemplary embodiment.

In the ionization device according to the first exemplary embodiment, a voltage is steadily applied to the ion extract electrode 10. Alternatively, a timing of the laser light irradiation and a timing of applying a voltage to the ion extract electrode 10 may be adjusted as desired. For example, a voltage may be applied to the ion extract electrode 10 for a given period of time immediately after the start of laser light irradiation. Then, unnecessary ions generated during a period in which the laser light is not radiated are not detected, and thus ions generated immediately after the laser light is radiated can be collected efficiently (see FIG. 3).

Second Exemplary Embodiment

An ionization device according to a second exemplary embodiment of the present invention has a configuration in which an end of the probe 3 is caused to vibrate. Points aside from the above are the same as those of the first exemplary embodiment.

Figure 2:
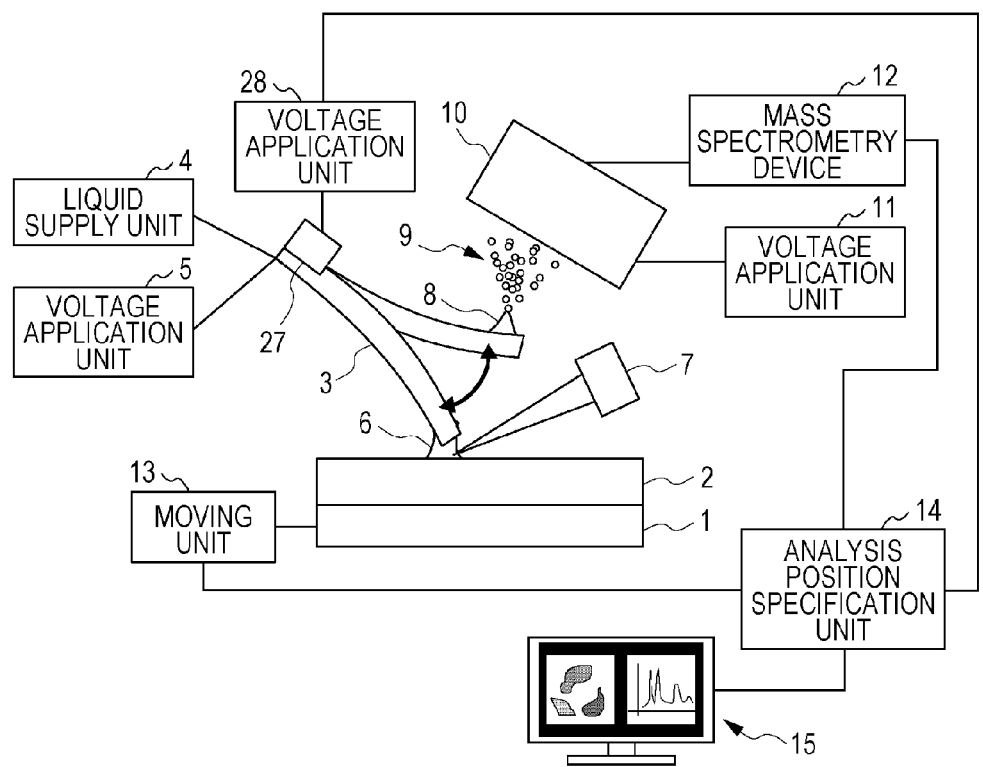
FIG. 2 is a schematic diagram illustrating an image generation system that includes an ionization device according to a second exemplary embodiment.

FIG. 2 is a schematic diagram illustrating the ionization device according to the second exemplary embodiment.

In the ionization device according to the second exemplary embodiment, a vibration unit 27 is provided on the probe 3 instead of the vibration unit 16 provided on the support 1. The vibration unit 27 is connected to a voltage application unit 28, which is then connected to the analysis position specification unit 14. The vibration unit 27 causes the probe 3 to vibrate in directions indicated by an arrow in FIG. 2.

The vibration unit 27 is formed by a piezoelectric element or a motor element and causes the probe 3 to vibrate. The amplitude of the vibration of the probe 3 is approximately a few tens of nanometers to a few hundreds of micrometers, and the frequency is approximately 10 Hz or more and up to 1 MHz.

The probe 3 vibrates continuously, and if the probe 3 makes contact with the sample 2 while vibrating, the liquid bridge 6 is formed between the probe 3 and the sample 2. If the probe 3 is separated from the sample 2 while vibrating, the liquid bridge 6 is not formed, but the Taylor cone 8 is generated and the liquid droplets 9 are sprayed. That is, formation of the liquid bridge 6 and generation of the liquid droplets 9 can be carried out separately by bringing the probe 3 and the sample 2 closer to or away from each other.

Then, if the probe 3 makes contact with the sample 2 while vibrating, the liquid bridge portion is irradiated with the laser light. If the probe 3 is separated from the sample 2 while vibrating and the liquid bridge 6 is not formed, since the liquid bridge 6 is not present, there is no liquid bridge portion to be irradiated with the laser light.

In this way, duration in which the probe 3 is in contact with the sample 2 is reduced since the probe 3 vibrates, and thus damage to the sample 2 to be caused by the probe 3 in association with the relative movement of the probe 3 and the sample 2 (i.e., relative movement in a scanning direction along the in-plane direction of the sample 2) can be suppressed. Further, reducing duration in which the liquid bridge 6 is formed leads to the reduction of the size of the liquid bridge 6, and thus the space where ionization takes place can be reduced in size.

In the ionization device according to the second exemplary embodiment, the vibration unit 27 causes the probe 3 to vibrate. Alternatively, spontaneous resonance of the probe 3 may be utilized without providing a vibration unit. This is considered to be possible if, for example, the size and the material of the probe 3, the size of the flow channel formed in the probe 3, the voltage applied thereto, and the flow rate of the solvent are set as follows.

Size of probe: 10 µm to 100 mm in length
Material: glass, stainless steel, silicon, PMMA
Size of flow channel: 1 µm$^2$ to 1 mm$^2$ in cross section
Applied voltage: 0 V to 10 kV
Flow rate of solvent: 1 nL to 100 µL per minute In the ionization device according to the second exemplary embodiment, the vibration unit 27 vibrates continuously. Alternatively, in an ionization device according to an exemplary embodiment of the present invention, the vibration unit 27 may vibrate intermittently as long as mass spectrometry on an ionized substance can be carried out. Here, "vibrating intermittently" refers to a case in which states where the probe 3 vibrates and is stopped are repeated alternately or a case in which the amplitude and/or the cycle of vibration of the probe 3 change repeatedly.

The vibration frequency to be set in the vibration unit 27 may be a resonance frequency or a non-resonance frequency.

In the ionization device according to the second exemplary embodiment, the leading end of the probe 3 vibrates between the sample 2 and the ion extract electrode 10. Alternatively, in an ionization device according to an exemplary embodiment of the present invention, the probe 3 may rotate in addition to vibrating. If the probe 3 is to rotate, a desired vibration in two axial directions that are orthogonal to each other may be given to the probe 3. In this case, the probe 3 vibrates in a combined wave pattern of two sine waves.

In the ionization device according to the second exemplary embodiment, the liquid supply unit 4 continuously supplies the solvent to a space between the probe 3 and the sample 2. Alternatively, in an ionization device according to an exemplary embodiment of the present invention, the liquid supply unit 4 may supply the solvent while the probe 3 is in close proximity to (or in contact with) the sample 2 and may stop supplying the solvent while the probe 3 is spaced apart from the sample 2. That is, the supply of the solvent and the vibration of the probe 3 may be synchronized.

The vibration of the probe 3 in the ionization device according to the second exemplary embodiment can be detected with various methods. For example, a side face of the probe 3 may be irradiated with the laser light, and displacement of reflected light from the probe 3 may be detected. As another example, an electric element for detecting a vibration may be connected to the probe 3, and distortion in the probe 3 may be detected on the basis of a change in electric resistance of the element. As yet another example, a magnetic material may be connected to the probe 3, and a change in an induced current that flows in a coil disposed close to the probe 3 may be detected.

In the ionization device according to the second exemplary embodiment, the liquid bridge 6 is irradiated with the laser light while the liquid bridge 6 is formed. Alternatively, the liquid bridge 6 may be irradiated with the laser light intermittently during a given period of time. That is, the liquid bridge 6 may be irradiated with the laser light for a given period of time, and then the irradiation may be stopped for another given period of time. For example, the ionization efficiency of a sample 2 in which both a substance that is easily decomposed by the laser light and a substance that is not easily decomposed by the laser light are present can be improved by pausing the irradiation of the laser light while the substance that is easily decomposed by the laser light undergoes ionization and by irradiating the sample 2 with the laser light while the substance that is not decomposed by the laser light undergoes ionization. Here, the frequency at which the liquid bridge 6 is irradiated with the laser light may be set to a desired frequency out of the total instances where the liquid bridge 6 is formed. For example, of the ten instances where the liquid bridge 6 is formed, the liquid bridge 6 may be irradiated with the laser light in any given five instances. In this manner, the number of instances where the liquid bridge 6 is formed and irradiated with the laser light and the number of instances where the liquid bridge 6 is formed but is not irradiated with the laser light within a given period of time can each be set to any desired value.

In the ionization device according to the second exemplary embodiment, synchronization of the formation of the liquid bridge 6 and the irradiation with the laser light can be achieved by adjusting the frequency and the phase of vibration of the probe 3 and the frequency and the phase of a control signal for the laser light. It is preferable to synchronize a signal obtained by monitoring the vibration of the probe 3 with a signal for controlling an irradiation timing of the laser light with a synchronization circuit.

Figure 4:
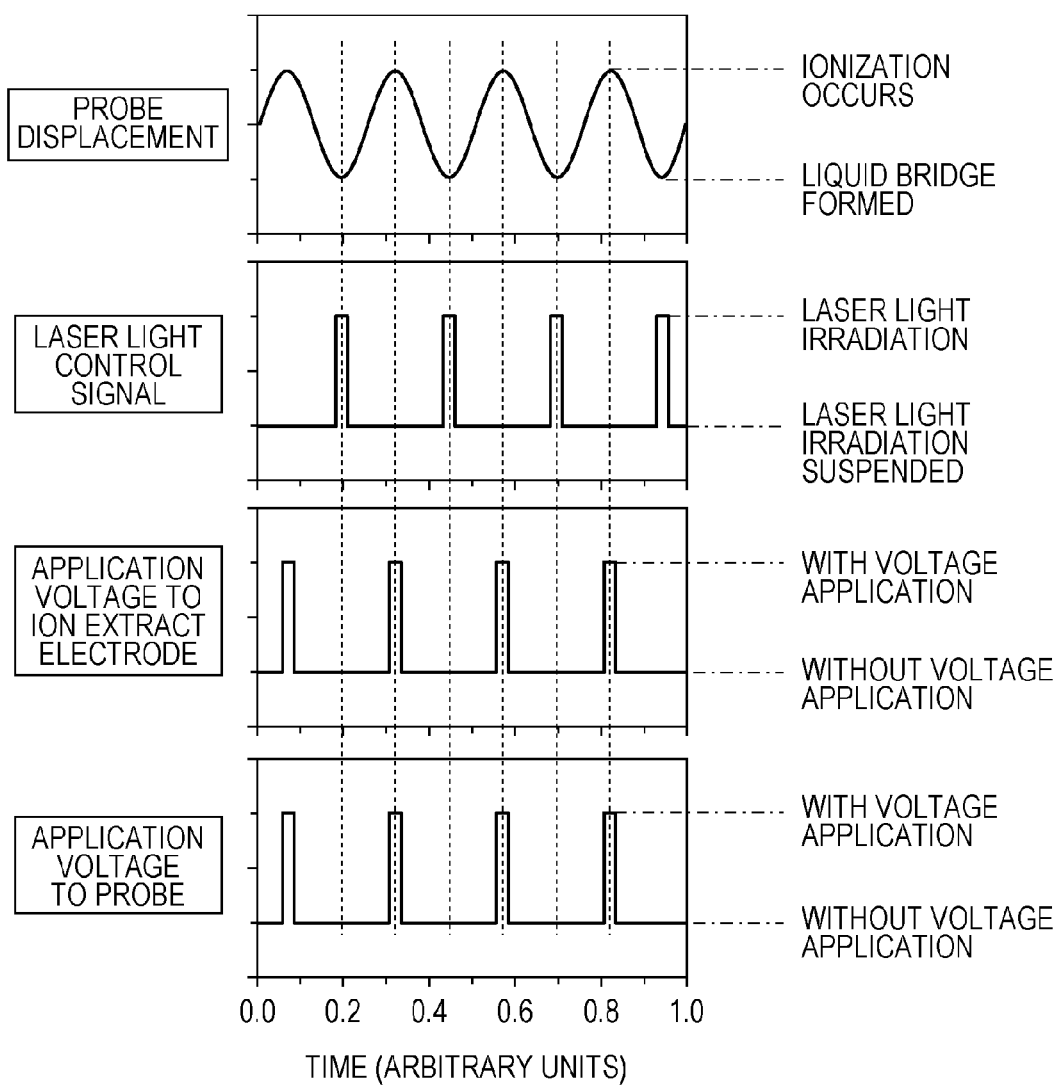
FIG. 4 is a schematic diagram illustrating timings of laser light irradiation and voltage application in the ionization device according to the second exemplary embodiment.

In the ionization device according to the second exemplary embodiment, a voltage is steadily applied to the ion extract electrode 10. Alternatively, the vibration timing of the probe 3 and the timing of applying a voltage to the ion extract electrode 10 may be synchronized. Then, unnecessary ions generated during a period in which the liquid bridge 6 is formed are not detected, and thus noise in the obtained measurement data can be reduced. Here, the synchronization of the vibration timing of the probe 3 with the timing of the laser light irradiation described above may be carried out additionally (see FIG. 4).

Synchronization of the formation of the liquid bridge 6, irradiation of the laser light, and the timing of applying a voltage to the ion extract electrode 10 can be achieved by adjusting the frequencies and the phases of the vibration of the probe 3, the control signal for the laser light, and the control signal for voltage application. These signals are preferably synchronized through a synchronization circuit.

Figure 5:
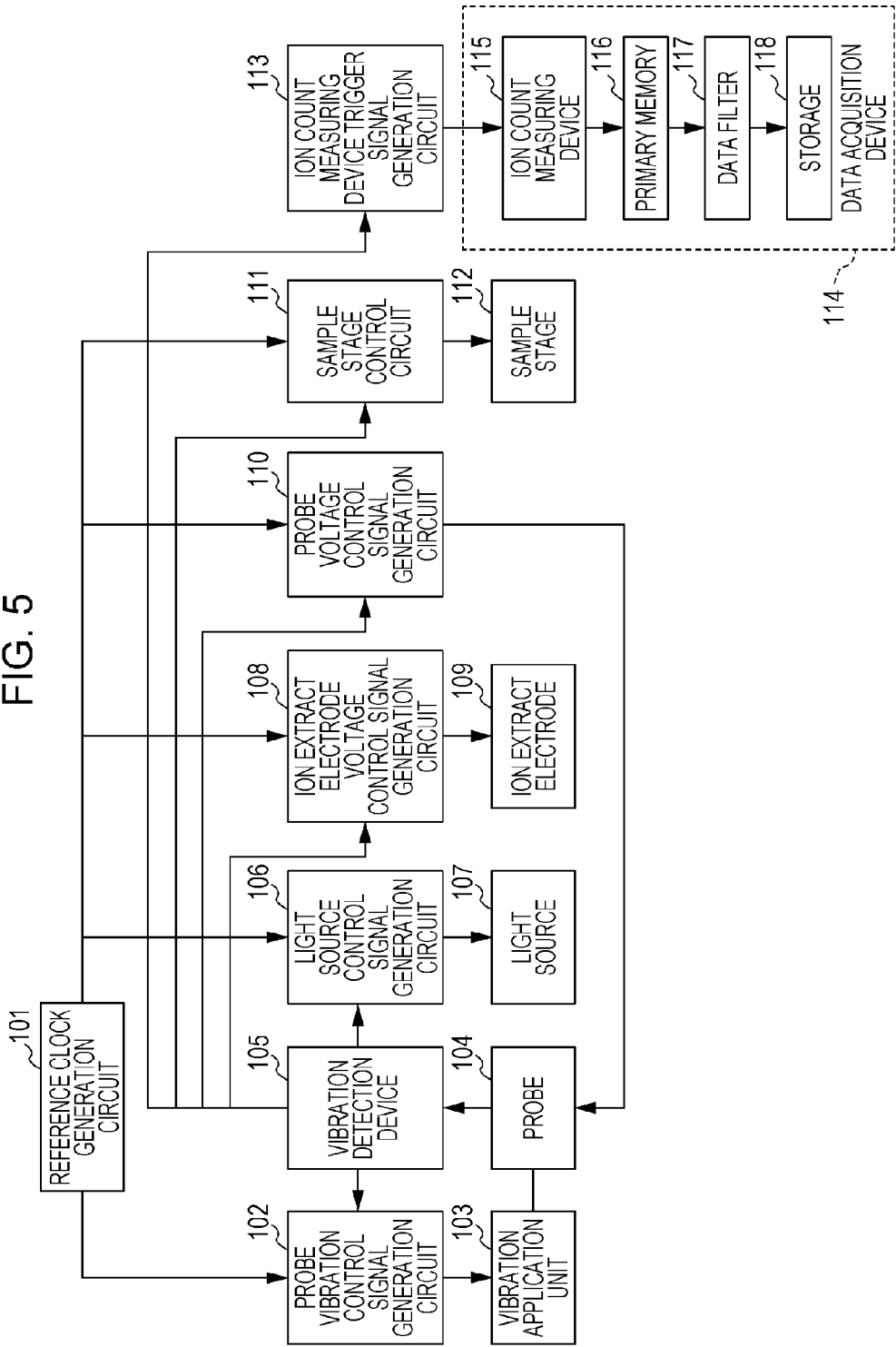
FIG. 5 is a schematic diagram illustrating a synchronization circuit of an ionization device according to an exemplary embodiment of the present invention.

In the ionization device according to the second exemplary embodiment, it is necessary to precisely adjust the timing at which a probe vibrates, the timing of laser light irradiation, application of a voltage to an extract electrode, a voltage applied to the probe, the timing at which a sample stage is moved, and acquisition and storage of data. An exemplary embodiment of a synchronization circuit for achieving the above is illustrated in FIG. 5.

The synchronization circuit of the exemplary embodiment includes a reference clock generation circuit 101, a probe vibration control signal generation circuit 102, a vibration application unit 103, a probe 104, a vibration detection device 105, a light source control signal generation circuit 106, a light source 107, an extract electrode voltage control signal generation circuit 108, an extract electrode 109, a probe voltage control signal generation circuit 110, a sample stage control circuit 111, a sample stage 112, an ion count measuring device trigger signal generation circuit 113, and a data acquisition device 114. The data acquisition device 114 includes an ion count measuring device 115, a primary memory 116, a data filter 117, and a storage 118.

Here, a case where a field programmable gate array (FPGA) or an application specific integrated circuit (ASIC) is used will be described as an example. The use of the FPGA or the ASIC makes it possible to implement a plurality of control circuits (i.e., reference clock generation circuit 101, probe vibration control signal generation circuit 102, light source control signal generation circuit 106, extract electrode voltage control signal generation circuit 108, probe voltage control signal generation circuit 110, sample stage control circuit 111) on an integrated circuit and to precisely adjust their control timings at high speed.

The probe vibration control signal generation circuit 102, the light source control signal generation circuit 106, the extract electrode voltage control signal generation circuit 108, the probe voltage control signal generation circuit 110, the sample stage control circuit 111, and the ion count measuring device trigger signal generation circuit 113 generate respective voltage signals and output the generated voltage signals to the vibration application unit 103, the light source 107, the extract electrode 109, the probe 104, the sample stage 112, and the ion count measuring device 115, respectively. Each of these voltage signals may be any one of a triangular wave, a square wave, a sine wave, and a cosine wave.

A feedback circuit is formed in the probe vibration control signal generation circuit 102 in order to bring a phase difference between a voltage signal obtained by detecting an actual vibration of the probe 104 and a voltage signal generated on the basis of a reference clock to zero, and driving this feedback circuit allows the probe 104 to vibrate at a constant frequency. The vibration detection device 105 is used to detect the actual vibration of the probe 104, and an output signal from the vibration detection device 105 is inputted to the feedback circuit in the probe vibration control signal generation circuit 102. Such a drive mechanism is known as a phase locked loop (PLL). Providing a delay compensation circuit within a circuit for the PLL makes it possible to generate a voltage signal having a desired delay time relative to a reference signal.

The output signal from the vibration detection device 105 is also inputted to the light source control signal generation circuit 106, the extract electrode voltage control signal generation circuit 108, the probe voltage control signal generation circuit 110, the sample stage control circuit 111, and the ion count measuring device trigger signal generation circuit 113. Certain times such as a timing at which the probe 104 forms a liquid bridge, a timing at which ionization occurs at the leading end of the probe 104, and a timing between the liquid bridge formation and the ionization are extracted on the basis of the inputted voltage signals, and driving of the devices that are connected to the respective circuits at the aforementioned timings are controlled. For example, a signal of displacement of the probe 104 in FIG. 4 serves as an output signal from the vibration detection device 105, and when this signal is inputted to the light source control signal generation circuit 106, the extract electrode voltage control signal generation circuit 108, the probe voltage control signal generation circuit 110, and the sample stage control circuit 111, a specific threshold voltage may be set. Then, a period in which a voltage falls below the threshold voltage can be set as a timing of forming a liquid bridge, or a period in which a voltage exceeds the threshold voltage can be set as a timing at which ionization occurs. Then, a timing at which a voltage is applied to the probe 104, a timing at which the light source 107 emits light, a timing at which a voltage is applied to the extract electrode 109, and a timing at which the sample stage 112 is moved are controlled so as to synchronize with the timings determined as described above. Further, using a signal from the reference clock generation circuit 101 makes it possible to quantitatively measure and to control a timing at which a voltage is applied to the probe 104, a timing at which the light source 107 emits light, a timing at which a voltage is applied to the extract electrode 109, and a timing at which the sample stage 112 is moved.

An output signal generated by the ion count measuring device trigger signal generation circuit 113 is inputted to the ion count measuring device 115 as a gate voltage signal. Generally, the ion count measuring device 115 intermittently receives a trigger signal from the mass spectrometer, and after receiving the trigger signal, the ion count measuring device 115 measures the number of ions that have reached the detector in the mass spectrometer. A trigger signal differs depending on the configuration of an ion separation unit in the mass spectrometer. In the exemplary embodiment, a quadrupole mass spectrometer, a TOF mass spectrometer, a magnetic field deflection mass spectrometer, or an ion trap mass spectrometer may be used as the mass spectrometer, and a specific timing may be used as a trigger signal for each instance of mass spectrometry.

For example, a signal indicating a timing of starting application of a high frequency voltage to a quadrupole electrode may be used as a trigger signal in the quadrupole mass spectrometer. In the TOF mass spectrometer, a signal indicating a timing of application of a pulse voltage for accelerating an ion in a device that measures the time of flight of the ion may be used as a trigger signal. In the magnetic field deflection mass spectrometer, a signal indicating a timing at which a magnetic field starts to be applied to a sector electrode may be used as a trigger signal. In the ion trap mass spectrometer, a signal indicating a timing at which an ion is introduced to an ion trap may be used as a trigger signal. Typically, the frequency of the pulse voltage in the TOF mass spectrometer is approximately a few kHz to a few tens of kHz, and the frequency of trapping ions in the ion trap mass spectrometer is approximately a few tens of Hz to a few kHz. Thus, the frequency is often higher than the vibration frequency of the probe 104.

In the exemplary embodiment, a gate voltage signal is outputted in synchronization with a timing at which ionization occurs at the leading end of the probe 104. The ion count measuring device 115 is configured to operate in accordance with a period in which the gate signal is outputted. Here, the gate signal is any one of a positive voltage, a negative voltage, and a zero voltage and differs depending on the ion count measuring device 115. The ion count measuring device 115 can be configured to operate only while ions are generated at the probe 104, and thus a noise signal is not measured while the liquid bridge is formed and during period from when the liquid bridge is formed until the ionization occurs. Therefore, a noise signal to be contained in a signal of measured data can be reduced.

Subsequently, a method for recording a voltage signal from the ion count measuring device 115 in the form of digital data will be described. A signal from the ion count measuring device 115 undergoes analog-to-digital conversion and is then temporarily stored in the primary memory 116. Measurement data that corresponds to the type of ions to be measured is selected and stored in the storage 118 such as a hard disk drive (HDD) and a solid state drive (SSD). This process of selecting the data is carried out through a program in the data filter 117, and the data is overwritten by new data in the memory. Since the data is stored in the storage 118 after being selected, the total amount of data can be reduced, and the selected data can be applied if the ion to be measured is determined in advance. Meanwhile, if an unknown ion is to be detected, the entire data obtained by the ion count measuring device 115 can be stored in the storage 118.

If a large area on a measurement target is to be measured, the sample stage 112 needs to be moved. The sample stage control circuit 111 generates a signal for controlling the position of the sample stage 112 on the basis of a reference clock and outputs the generated signal to the sample stage 112. At this point, by measuring a timing at which ionization occurs at the leading end of the probe 104 and the number of instances of ionization within a given period of time on the basis of the signal from the vibration detection device 105, the number of instances of ionization per position on a sample can be kept constant. Acquisition and storage of the data can be carried out successively while moving the sample stage 112. Thus, pieces of two-dimensional data on the measurement target can be stored successively.

Thus far, a case where the signal generation circuits generate respective output signals relative to a threshold has been described, but the exemplary embodiments are not limited thereto. A common signal generation circuit may be provided separately, and the common signal generation circuit may extract specific times on the basis of a signal from the vibration detection device 105. Then, the common signal generation circuit may input a voltage signal corresponding to the extracted times to the light source control signal generation circuit 106, the extract electrode voltage control signal generation circuit 108, the probe voltage control signal generation circuit 110, the sample stage control circuit 111, and the ion count measuring device trigger signal generation circuit 113.

In the exemplary embodiment, a synchronization method in a case where the probe 104 vibrates has been described. Alternatively, if the probe 104 is paused, the probe vibration control signal generation circuit 102, the vibration application device 103, and the vibration detection device 105 that relate to the vibration of the probe 104 may be stopped, and various control signals may be generated using signals from the reference clock generation circuit 101 in the respective control circuits.

According to an exemplary embodiment of the present invention, an ion analysis device that excels in ionization in an atmospheric pressure environment can be provided. Further, since the ion analysis device according to the exemplary embodiment of the present invention is configured to irradiate the liquid bridge portion with the laser light, a substance in a sample that does not easily dissolve in a solvent can be allowed to dissolve more easily, or a solute dissolved in a solvent can easily undergo a photochemical reaction.

In foregoing description, specific details are set forth in order to provide a thorough understanding of the embodiments disclosed. In certain instances, well-known methods, procedures, components and circuits have not been described in detail as not to unnecessarily lengthen the present disclosure. Some embodiments or diagrams of the present invention may be practiced on a computer system that includes, in general, one or a plurality of microprocessors for processing information and instructions.

As will be appreciated by those of ordinary skill in the art, certain aspects of the embodiments disclosed herein may be embodied as a system, a method or a computer program product. Accordingly, some aspects of the embodiments may take the form of an entirely hardware product, or combination of software and hardware products; these may all be generally referred herein as a "unit", "circuit", "module" or "system". Further, some embodiments may take the form of a computer program product embodied in any non-transitory computer-readable storage medium having computer-usable program code stored therein. For example, some embodiments described above with reference to flowchart illustrations and/or block diagrams of methods, apparatus (systems) and computer program products can be implemented by computer program instructions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-197209, filed Sep. 7, 2012, which is hereby incorporated by reference herein in its entirety.

What is claimed is:

1. An ionization device, comprising:
a support configured to support a sample;
a probe configured to determine a portion of the sample to be ionized;
an irradiation unit configured to emit laser light, the irradiation unit being disposed to irradiate with the laser light a liquid bridge portion between the sample and the probe;
an extract electrode configured to extract ions obtained by ionizing the sample;
a liquid supply unit configured to supply a liquid to a region of the sample; and
an electric field generation unit configured to generate an electric field between a portion of the probe that is in contact with the liquid bridge portion and the extract electrode.

2. The ionization device according to claim 1, further comprising:
a vibration unit configured to cyclically change a relative distance between the probe and the sample,
wherein while the liquid bridge portion is not formed as the probe and the sample are spaced apart from each other, the liquid on one of the probe and the sample is not irradiated with the laser light, and
wherein while the liquid bridge portion is formed as the probe and the sample are close to each other, the liquid bridge portion is irradiated with the laser light.

3. The ionization device according to claim 1, further comprising:
a drive unit configured to drive the laser light irradiation unit to emit pulsed laser light.

4. The ionization device according to claim 1, further comprising:
a moving unit configured to change the position of the liquid bridge portion relative to the sample.

5. The ionization device according to claim 4, wherein the moving unit is configured to move the support.

6. The ionization device according to claim 4, wherein the moving unit is configured to move the sample while retaining a positional relationship between the irradiation unit and the probe.

7. The ionization device according to claim 1, further comprising:
a synchronization circuit configured to synchronize a timing of laser light irradiation with a timing at which one of the sample and the probe vibrates.

8. The ionization device according to claim 1, further comprising:
a synchronization circuit configured to synchronize a timing of laser light irradiation with a timing at which an electric field is generated between a portion that is in contact with the liquid bridge portion and the extract electrode.

9. The ionization device according to claim 1, further comprising:
a synchronization circuit configured to synchronize a timing of laser light irradiation with an operation timing of an ion count measuring device connected to the ionization device.

10. The ionization device according to claim 1, further comprising:
a synchronization circuit configured to synchronize a timing of laser light irradiation with a timing at which a voltage is applied to an ion extract electrode of the ionization device.

11. The ionization device according to claim 1, further comprising:
a synchronization circuit configured to synchronize a timing of laser light irradiation with at least two of a timing at which one of the sample and the probe vibrates, a timing at which an electric field is generated between a portion that is in contact with the liquid bridge portion and the extract electrode, an operation timing of an ion count measuring device connected to the ionization device, and a timing at which a voltage is applied to the ion extract electrode of the ionization device.

12. A mass spectrometer, comprising:
the ionization device according to claim 1 serving as an ionization unit; and
a mass spectrometry device configured to analyze a mass-to-charge ratio of the extracted ions obtained by ionizing the sample.

13. An image generation system, comprising:
the mass spectrometer according to claim 12; and
an image information generation device that includes
an image generation unit configured to generate image information to display an image of a component distribution of a substance contained in the sample on the basis of mass information obtained through analysis by the mass spectrometer and positional information on the region of the sample, and
an output unit configured to output the image information to a display device.

14. A method for analyzing a sample, the method comprising:
forming a liquid bridge portion that links a probe and a sample with a liquid disposed on a surface of the sample;
irradiating the liquid bridge portion with laser light; and
spraying the liquid on the probe to carry out mass spectrometry on an ionized substance contained in the sample.

15. The method according to claim 14, further comprising:
moving the probe relative to the surface of the sample.

16. The method according to claim 14, wherein a mass spectrometry image is obtained on the basis of information obtained by the mass spectrometry carried out at a plurality of positions on the sample.

* * * * *